United States Patent
Mahoney et al.

(10) Patent No.: US 10,818,388 B2
(45) Date of Patent: *Oct. 27, 2020

(54) SYSTEMS AND METHODS FOR ADMINISTRATION OF PRESCRIPTION DRUG BENEFITS

(71) Applicant: Quest Diagnostics Investments Inc., Wilmington, DE (US)

(72) Inventors: Richard A. Mahoney, Cincinnati, OH (US); Thomas R. Wagner, Cincinnati, OH (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 37 days.

This patent is subject to a terminal disclaimer.

(21) Appl. No.: 15/905,514

(22) Filed: Feb. 26, 2018

(65) Prior Publication Data

US 2018/0182477 A1 Jun. 28, 2018

Related U.S. Application Data

(63) Continuation of application No. 14/158,725, filed on Jan. 17, 2014, now abandoned, which is a
(Continued)

(51) Int. Cl.
*G16H 20/00* (2018.01)
*G06Q 30/06* (2012.01)
(Continued)

(52) U.S. Cl.
CPC .......... *G16H 20/00* (2018.01); *G06F 19/328* (2013.01); *G06F 19/3456* (2013.01);
(Continued)

(58) Field of Classification Search
CPC ........ G16H 20/00; G16H 80/00; G16H 20/10; G06F 19/3456; G06F 19/328; G06Q 50/22; G06Q 40/08; G06Q 30/06; G06Q 50/24

See application file for complete search history.

(56) References Cited

U.S. PATENT DOCUMENTS

| 5,845,255 A | 12/1998 | Mayaud |
| 2001/0001144 A1* | 5/2001 | Kapp .................... G06F 19/326 705/3 |

(Continued)

*Primary Examiner* — Linh Giang Le
(74) *Attorney, Agent, or Firm* — Jon E. Gordon; Haug Partners LLP

(57) ABSTRACT

The invention relates to the administration of prescription drug formulary information. A list of drugs that a particular prescription drug plan will pay for in whole or in part is called a formulary. The invention involves the use of information and customizable rules associated with formularies, combined with information from patient medical records, to generate custom, dynamic formularies applicable to specific patients, groups of patients, or both. Depending on the choice of rules and the other information, this may help payers control prescription drug costs by encouraging the use of less-expensive drugs when medically appropriate, but without impairing the freedom of prescribers to prescribe specific drugs according to their professional judgments. Some embodiments may also be adapted to generate and store data about the use and functioning of the embodiments or aspects of them and to generate reports containing some or all such data in response to queries.

11 Claims, 10 Drawing Sheets

Related U.S. Application Data continuation of application No. 13/007,067, filed on Jan. 14, 2011, now Pat. No. 8,635,089, which is a continuation of application No. 11/347,144, filed on Feb. 3, 2006, now Pat. No. 7,895,060, which is a continuation of application No. 11/112,696, filed on Apr. 21, 2005, now abandoned.

(51) Int. Cl.
*G06Q 40/08* (2012.01)
*G06Q 50/22* (2018.01)
*G06F 19/00* (2018.01)
*G06Q 50/24* (2012.01)
*G16H 20/10* (2018.01)
*G16H 80/00* (2018.01)

(52) U.S. Cl.
CPC .............. *G06Q 30/06* (2013.01); *G06Q 40/08* (2013.01); *G06Q 50/22* (2013.01); *G06Q 50/24* (2013.01); *G16H 20/10* (2018.01); *G16H 80/00* (2018.01)

(56) References Cited

U.S. PATENT DOCUMENTS

| | | |
|---|---|---|
| 2001/0037216 A1 | 11/2001 | Oscar et al. |
| 2002/0042725 A1 | 4/2002 | Mayaud |
| 2002/0138303 A1 | 9/2002 | Enos et al. |
| 2003/0065537 A1* | 4/2003 | Evans .................. G06F 19/326 705/2 |
| 2004/0006491 A1 | 1/2004 | Brown et al. |

\* cited by examiner

FIG. 9

Patient Information — Edit
401 — TEMPLE, ERMA 3/9/1957
123 Lincoln Rd.
Indianapolis, IN 46202

Patient Insurance — More
404 — ESI is the pharmacy benefit
403 — administrator for this patient.
Plan Name  RxHUB TESTING
         A02
Plan #   A02
Card ID  A02V
         11111112
         405  406

Patient Problem List — Edit
409 — NONE

Patient Allergies — Edit
411 — No allergies have been selected for this patient.

Medication History — More
eRx History    PBM History
417 — Medication    Days Ago
Prozac           7
419 — Lipitor    9
         415

Select Medication
                [            ] 427
                [///SEARCH] 428  [///CANCEL] 429

Medication List — 432
• Amoxil
• Cordarone
• Coumadin
• Crofab
• Crolom
• Delonide
• Diflucan
• Loroxide
• Lortab 10
• Micatin
• Penicillin
• Viagra
※ Zocor Per payer rule Refills not covered until lipid profile completed — 435

*Every effort has been made to ensure that the information provided by Cerner Multum, Inc. is accurate, up-to-date, and complete, but no guarantee is made to that effect. In addition, the drug information contained herein may be time sensitive. Multum's drug information does not endorse drugs, diagnose patients or recommend therapy. Multum's drug information is an informational resource designed to assist licensed healthcare practitioners in caring for their patients and/or to serve end users

425

SYSTEMS AND METHODS FOR ADMINISTRATION OF PRESCRIPTION DRUG BENEFITS

CROSS-REFERENCE TO RELATED APPLICATION

This application is a continuation of U.S. patent application Ser. No. 14/158,725, filed 17 Jan. 2014 and titled "Systems and Methods for Administration of Prescription Drug Benefits", which is a continuation of U.S. patent application Ser. No. 13/007,067, filed 14 Jan. 2011 and titled "Systems and Methods for Administration of Prescription Drug Benefits", now U.S. Pat. No. 8,635,089, which is a continuation of U.S. patent application Ser. No. 11/347,144, filed 3 Feb. 2006 and titled "Systems and Methods for Administration of Prescription Drug Benefits", now U.S. Pat. No. 7,895,060, which is a continuation of U.S. patent application Ser. No. 11/112,696, filed 21 Apr. 2005 and titled "Systems and Methods for Administration of Prescription Drug Benefits", now abandoned, which is incorporated by reference herein.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent files or records, but otherwise reserves all copyrights whatsoever.

BACKGROUND

The present invention relates to administering prescription formulary data associated with various entities, and more particularly to providing customized or dynamically generated or adjusted formulary data based on the application of one or more rules to formulary data associated with the various entities.

As third-party payers have come to bear an increasing share of the cost of prescription drugs, they have sought ways to manage those costs and to save money through efficiencies in administering their programs. Third-party payers comprise employers and governments. Employees or patients also pay for prescriptions, directly in the form of co-payments or simply by paying the retail cost of prescription drugs and indirectly through their contributions to the cost of prescription drug coverage. (The term "payer," as used herein, thus comprises employers, employees, and governments.)

Payers typically delegate administration of their payment systems to organizations called Pharmacy Benefit Managers (PBMs), which are intermediaries between payers on the one hand and patients and pharmacies on the other. Payers engage PBMs to administer their plans and to handle billing and payment.

To help control costs, payers sometimes limit the drugs that they will pay for. With the help of the PBMs, payers create lists of the medications that a managed health (or prescription drug) plan will pay for and the amounts that they will pay for each one. The lists may also include information about alternatives to unlisted drugs. In either case, such a list is called a formulary.

PBMs, in conjunction with payers, provide formularies to payers and to information and prescription aggregators, which operate as third-party electronic sources of formulary information. Examples of information and prescription aggregators are organizations such as Medimedia and RxHub. RxHub, for example, is an organization created by PBMs to help control payers' expenses. It receives formulary data for numerous health plans and then makes these formularies available to third parties. The formularies provided by RxHub are currently updated weekly and represent a substantial portion of formularies available in the U.S.

There are other content aggregators as well, which obtain formulary data from PBMs and make it available to others. For example, the Council for Affordable Quality Healthcare (CAQH) has created standards for electronically publishing formulary information. CAQH-formatted information is available through RxHub. Some sources of formularies operate independently of information and prescription aggregators yet seek to make their formulary information available electronically as well.

There are thousands of payers, and each has its own formularies. Each payer typically has numerous plans, and each plan can have a unique formulary. There are thus thousands of plans and formularies.

A payer may cover drugs at different levels depending on the plan that covers a particular person. Within a plan, also, there are likely tiers of coverage: the plan participant may have to pay more or less for drugs depending on the tiers in which the drugs are. For example, a formulary may specify that the co-payment is ten dollars for generic drugs, but thirty dollars for branded ones.

Formulary information can affect decisions in the drug prescribing process. Current formularies are created based on drugs and coverage amounts specified in particular plans.

The coming of electronic prescribing, which is an application that helps prescribers use patient and formulary information when they create prescriptions electronically, has facilitated the use of information in formularies in the prescribing process. For example, a physician's selection of a medication in an electronic prescribing system loaded with the appropriate formularies triggers a query of the formulary to see if that specific medication is present. The query will provide the physician with information regarding the status of a medication as being on or off formulary. Depending on the data available, levels of co-payment can also be presented. The physician can write the prescription of the medication originally selected or can select a different medication.

BRIEF SUMMARY

Embodiments of the invention generate a formulary or set of formulary data which is based on a first formulary or first set of formulary data and on other information which changes (e.g., updates, revises or adds to, or customizes) information in the first formulary or first set of formulary data. This may be described as evidence-based administration of formularies.

For example, the first formulary or first set of formulary data may be that of an existing formulary or set of existing formulary data, which, once created, remains in effect for a group of plan participants until replaced by another formulary provided from time to time or periodically, typically to update the prior formulary. For example, the first formulary or set of formulary data may apply to all members of a particular plan. Thus, prescribers use plan-wide, fixed formulary data when prescribing drugs for individual plan members. Such formularies, currently used in drug prescribing processes, are relatively static, of general application, or both.

The formulary or set of formulary data thus generated is a second formulary or second set of formulary data, which is an adjusted formulary or set of formulary data, as compared to the first or existing formulary or set of formulary data. Second or adjusted formularies or sets of formulary data provided by embodiments of the invention may be created on a use or request basis, and/or may be customized for use with a specific patient or patients or for patients with the same or a similar medical condition, e.g., high blood pressure. ("First formulary," "first set of formulary data," "existing formulary," and "set of existing formulary data" are used interchangeably herein unless the context indicates otherwise. Similarly, "second formulary," "second set of formulary data," "adjusted formulary," and "set of adjusted formulary data" are used interchangeably herein unless the context indicates otherwise. Also, "information" and "data" are used interchangeably herein unless the context indicates otherwise.)

The other information referred to above may include any suitable information, for example, information relevant to the prescribing process, plan coverage, or both, among other things. For example, such information may include information associated with patient medical records, updated formulary information, and other information.

In an embodiment of the invention, an adjusted formulary is provided using an existing formulary, such other information, and rules by which the existing formulary is adjusted based on the other information and the rules.

In an embodiment of the invention, an adjusted formulary is created as part of or in response to a process that uses the adjusted formulary, or in response to a request for the formulary in connection with an anticipated use of the formulary, for example, during a drug prescribing process. Such an adjusted formulary may be referred to as a dynamically created or dynamically adjusted formulary.

In an embodiment of the invention, an adjusted formulary is customized for use with a particular patient or group of patients, possibly based, for example, on patient medical records data. For example, a custom adjusted formulary may be provided for patients with high blood pressure or for a specific patient for whom a prescription is being written.

In an embodiment of the invention, an adjusted formulary is provided that is both dynamically created or adjusted and customized.

An adjusted formulary provided by embodiments of the invention may provide adjustment for patient risk factors and/or financial risk factors of payees. An example of a patient risk factor is the risk that a patient will be prescribed a drug to which the patient has a known drug interaction. An example of a financial risk factor is that a patient will be prescribed a drug for no information in the patient's medical records demonstrates a need or where a generic may be used instead of a branded drug. Therefore, "risk" is used in a broad sense and encompasses various risks associated with providing health care. An adjusted formulary provided by embodiments of the invention may be referred to as a dynamic risk-adjusted formulary.

In an embodiment of the invention, a Dynamic Risk-Adjusted Formulary Management (DRAFM) process is provided that augments static formularies with clinical data to provide dynamic formularies based on the rules provided by payers and physicians and available patient data. The Dynamic Risk-Adjusted Formulary Manager comprises a set of technology components that will allow physicians, payers, or PBMs to specify rules that will help provide clinicians with formularies that are based on specific conditions of patients.

In an embodiment of the invention, the workflow may start when a request for a formulary is made and the original formulary is run through the Dynamic Risk-Adjusted Formulary Manager. The DRAFM checks to see if any rules apply to the formulary being prescribed. The rules are entered through a Dynamic Risk-Adjusted Rules Administrator, which may be a web-based tool provided to physicians, payers, PBMs, and employers. If a rule exists, the DRAFM retrieves the appropriate clinical data and verifies it against the rule conditions. The modified formulary is the output of the workflow. The Dynamic Risk-Adjusted Formulary Manager will request data needed to verify any applicable rules. When a rule requires a change in the original formulary, the rule number and text describing the rule may be provided, so it can be recorded on the prescription.

An adjusted or dynamic risk-adjusted formulary may provide PBMs and/or payers with the ability to adjust their formularies based on clinical information. PBMs and/or payers can create sets of rules that describe the circumstances under which they will pay for different prescriptions. These rules can consider information in a patient's electronic medical records, such as a patient's height, weight, age, and test results. A run-time engine evaluates these rules and decides at the time of prescribing whether to pay for a drug. Possible outcomes of this evaluation may comprise:

Giving feedback to the physician;
Displaying a message warning that the payer may not pay for the drug; and
Displaying a message that payer will pay for the drug for only 1 month (or other length of time).

A custom formulary can thus be created for each patient, the contents of which are determined at the time the prescription is created, in accordance with an embodiment of the invention.

For example, consider a situation in which a physician wants to prescribe Lipitor, a drug for lowering blood cholesterol levels, but the patient's chart does not contain results of any cholesterol tests. A payer may set rules that, in this circumstance, mean that it will not pay for Lipitor until the patient has a cholesterol test. Or the rules may specify that one month's supply of the drug will be covered but that no renewal will be approved unless the patent has the test.

Rules may also be condition-based, taking into account the tests done and the level of specificity in the diagnosis. According to an international standard, diagnoses are assigned codes that reflect the condition and the specificity with which it has been diagnosed. For example, according to the standard, a diagnosis of acoustic neuroma (a kind of non-cancerous brain tumor) is associated with code number 225.1. A benign tumor without further details, in contrast, receives the code number 225. Approval of a drug for payment may be made contingent on the inclusion of a code indicating a condition or class or conditions. Additionally or alternatively, approval may be made contingent on the degree of specificity implicit in the code number.

Other rules may consider the duration of the prescription. For example, renewals might be limited to a total of six months. Other plans may want to use other criteria, such as offering different formularies to smokers and non-smokers. The rules could also specify different tiers of payments.

Whatever the rules that the PBMS and/or payers choose, embodiments of DRAFM check the patient's data and then apply the appropriate rules.

In another embodiment, an adjusted formulary can be integrated with a product that connects an electronic prescribing application with the delivery of prescriptions to pharmacies. In the embodiment, rules can provide the basis for billing the prescription to a payer, which can help ensure that the appropriate payments will be sent to pharmacies.

An embodiment of the invention provides for gathering and/or processing statistical data—comprising the data available for providing a second set of formulary data from a first set, the second set of formulary data, and/or statistics about the operation of the embodiment and/or any aspect or aspects of it—and/or for generation of reports comprising such statistical data or statistical data derived from such data and other data. The reports can contain statistical data about any aspect of the use or operation of a dynamic formulary system, comprising the number of prescriptions checked against dynamic formularies, the number of prescriptions for on-formulary drugs, the number of prescriptions for off-formulary drugs, the number of times prescribers switched from off-formulary drugs to on-formulary drugs, the numbers of prescriptions sent to any one or more pharmacies, any costs or savings associated with use of the dynamic formulary, or any or all of these aspects. Depending on the embodiment, a report or reports may also comprise statistical data associated with any other aspect of the operation or use of a dynamic formulary or its implementing systems or its individual components. Depending on the embodiment, any numbers or other statistical data included in a report may be sorted, broken down, or both according to criteria that comprise, for example, patient, patient's condition, prescriber, PBM, plan, payer, drug, geographic area, or any groups or classes of these criteria, or any or all of these criteria, groups, or classes.

Reports may comprise data generated, collected, or both incidental to the performance of any function of the invention. Embodiments of the invention may be adapted so as to record the details of any event or activity that may be potentially desirable for inclusion in one or more reports. Some such embodiments may be adapted to be capable of collecting data at certain events and/or activities but also further adapted to collect such data only at a user-configurable subset of those events and/or activities.

Depending on the embodiment, some or all functions, modules, or subsystems of the invention may be adapted to accumulate or generate data for inclusion in reports, and such data may be stored in a database or by other means. Such data may be extracted by queries, and the generation of reports may be governed by query languages, scripting languages, or other means for specifying the content and presentation of reports and generating such reports. Depending on the embodiment, the nature of the reports available to the end user may be defined by the implementers of the invention, defined by one or more end-users, or both.

BRIEF DESCRIPTION OF THE DRAWINGS

The invention is illustrated in the figures of the accompanying drawings, which are meant to be exemplary and not limiting, and in which like references are intended to refer to like or corresponding parts.

FIG. 9 depicts a user interface screen for use in selecting a drug in the course of preparing electronic prescriptions according to an embodiment of the invention.

DETAILED DESCRIPTION OF THE PREFERRED EMBODIMENTS

Figure 1:
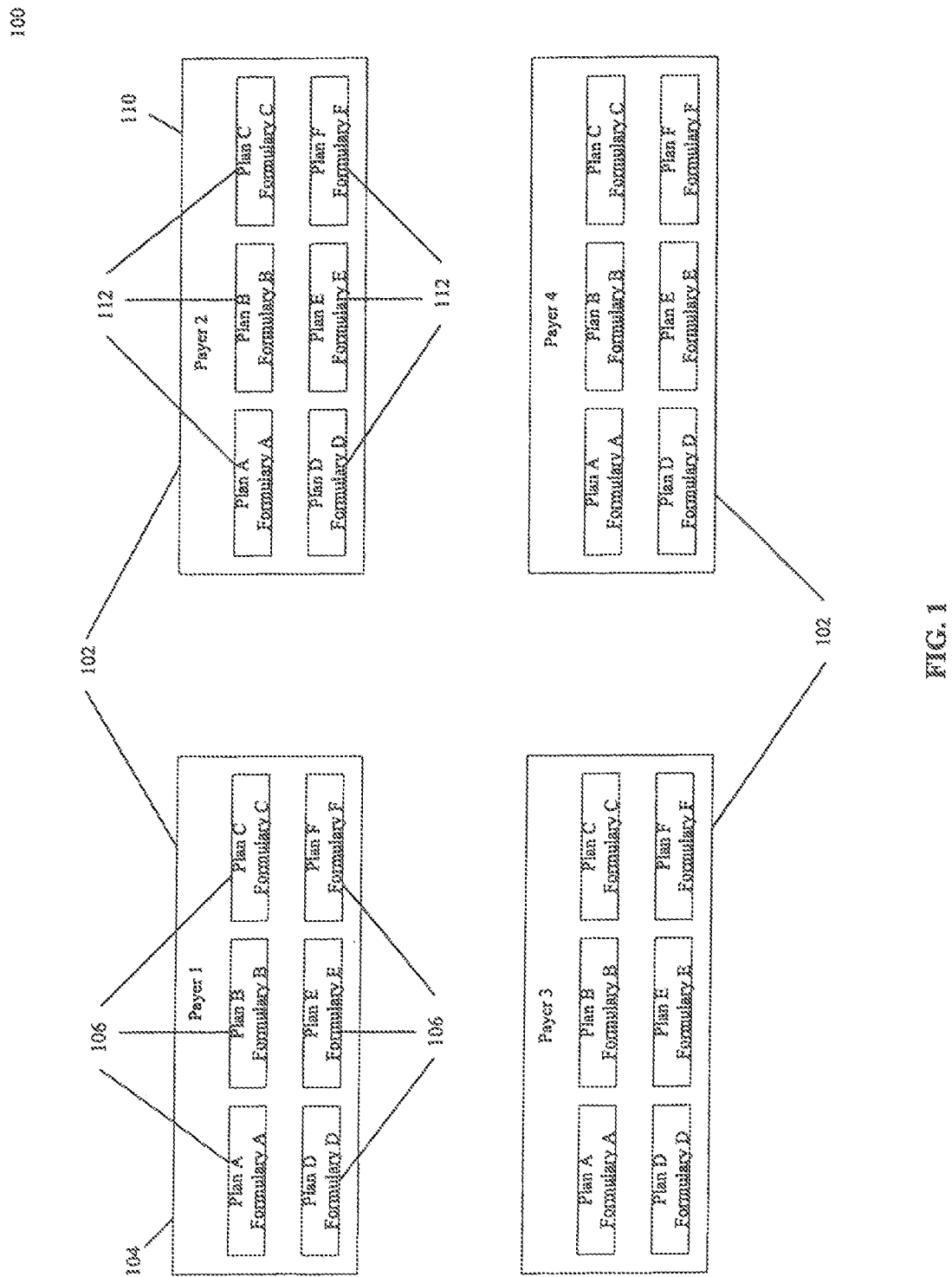
FIG. 1 is a diagram illustrating the organization of formularies by payers.

A formulary is a list of drugs based on a specific payer and a specific plan. FIG. 1 illustrates the relationship between payers, plans, and formularies. The FIG. 100 shows four payers 102. Payer 1 (referenced by 104) offers six different plans 106. If, for example, Payer 1 is an employer, it may offer its employees six different plans 106, each offering different benefits and requiring a different contribution from the employee. Each of these plans 106 is associated with its own distinct formulary.

Similarly, Payer 2 (referenced by 110) offers six different plans 112, and each plan is associated with its own distinct formulary.

These formularies exist because formulary management is a significant benefit to payer organizations. The payers make available the different formulary options to meet both the financial needs of an employer and the benefit needs of employees. But since there are thousands of payers and each payer can have several plans, there are thus thousands of plans and formularies, all of which need to be managed.

Figure 2:
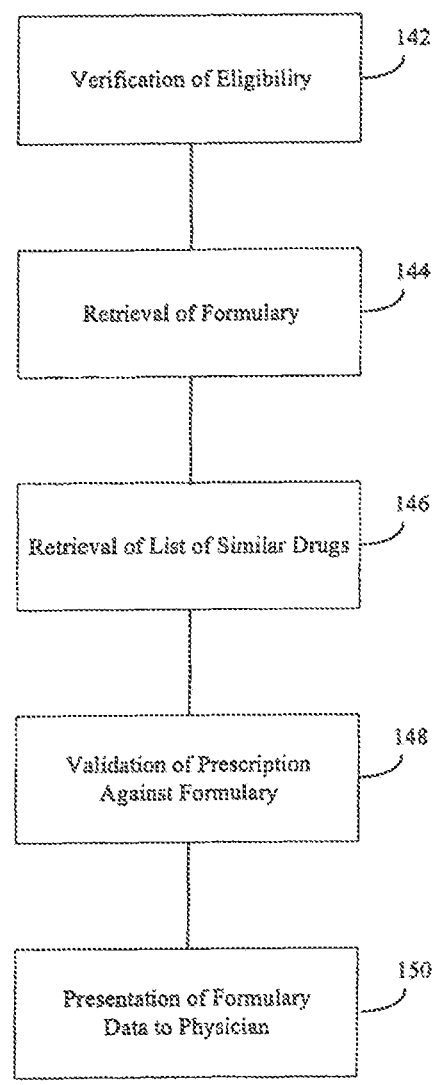
FIG. 2 is a diagram that depicts the flow of static formulary data used with electronic prescribing.

Electronic prescribing has been helpful. FIG. 2 illustrates how static formularies work with the generation 140 of an electronic prescription for a drug for a patient. In block 142, the patient's eligibility for a particular plan is checked against one or more databases. If the patient is eligible, then the appropriate formulary for that plan is retrieved in block 144.

From one or more databases, from the formulary, or both, a list of drugs similar to the prescribed drug is retrieved in block 146. A "similar" drug here is a drug with some or all of the same indications as the prescribed drug, or a drug that is prescribed in similar circumstances.

In block 148, the validity of the prescription is checked against the formulary. Finally, in block 150, the results of the other blocks are displayed to the physician. In some implementations of electronic prescribing, the physician will be told that the prescribed drug is or is not on the formulary and will also be shown the list of the similar drugs that were identified in block 146. If the information is available to the electronic prescribing system, the physician may also be told what co-payment will be required for the drug.

A physician can write a prescription for any drug, whether listed on the formulary or not, or can select a different drug. A formulary is an indicator of payment by a health plan, not a mandate as to the medication the physician can prescribe. It will be appreciated that the formulary consulted during the process 140 is static.

Figure 3:
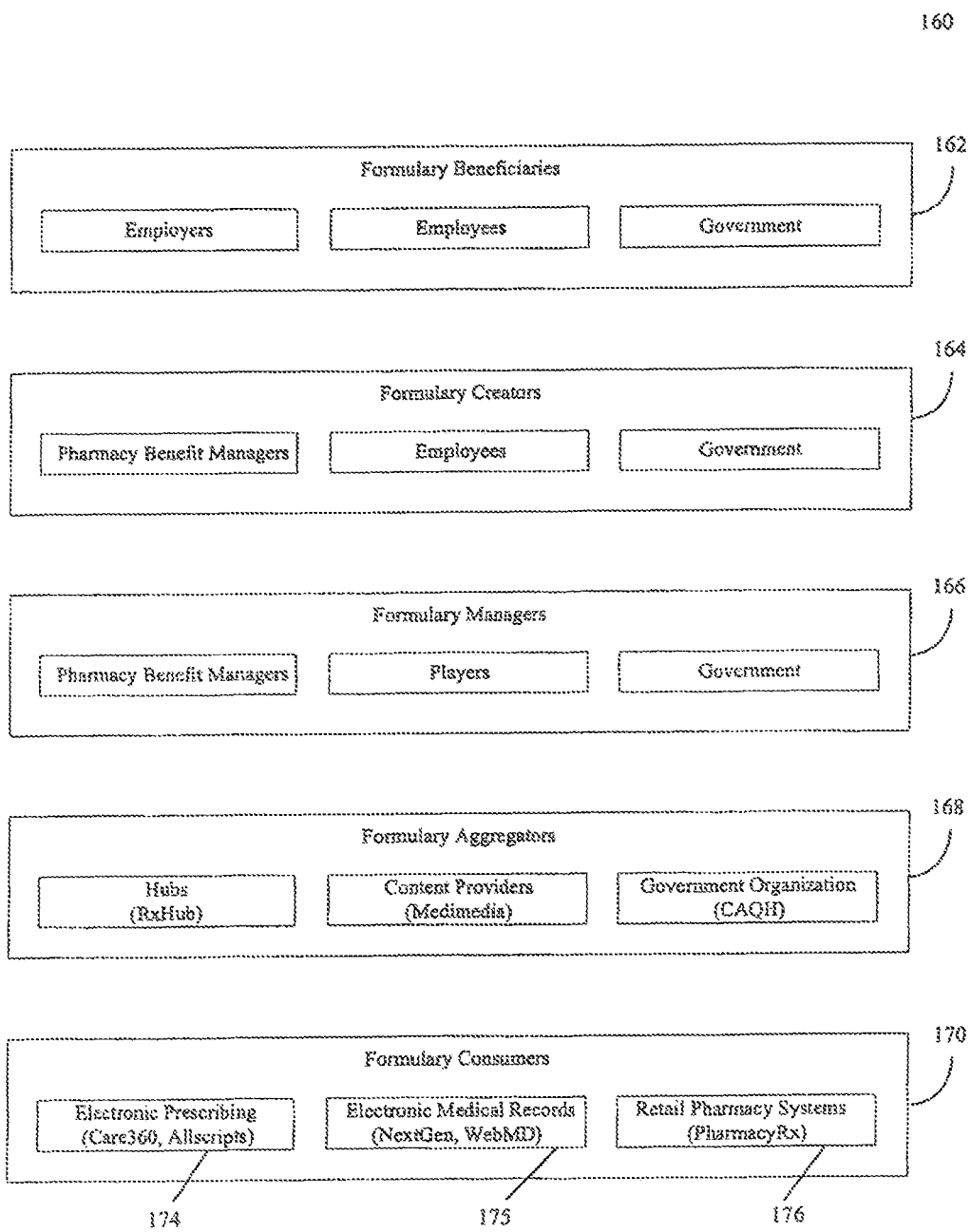
FIG. 3 is a diagram illustrating the creation and distribution of static formularies.

FIG. 3 depicts the various roles in which different entities interact with a formulary during its lifecycle 160.

Block 162 depicts the beneficiaries of a formulary. That is to say, these are the entities that benefit from the existence of a formulary: employers, government, and employees. Depending upon the needs of the beneficiaries 162, the formulary creators 164 may comprise PBMs, governments, and other payers.

Once a formulary has been created, it is administered by a formulary manager 166. Most formularies are managed for the beneficiaries 162 with the help of Pharmacy Benefit Managers (PBMs). The PBMs commonly make formulary information available to aggregators 168. These aggregators may comprise information aggregation companies (such as Medimedia) and drug aggregation hubs (RxHub) PBMs also make the formularies available to payers.

Once distributed by one or more of the aggregators 168, a formulary is available for use by consumers 170. One such consumer is an electronic prescribing system 174. Using a prescribing system loaded with the appropriate static formularies, a physician's selection of a drug for a patient triggers a request of the formulary based on the payer and plan, as depicted in block 144 of FIG. 2. Other consumers of formulary data may include providers 175 of electronic medical records and retail pharmacies 176.

Figure 4:
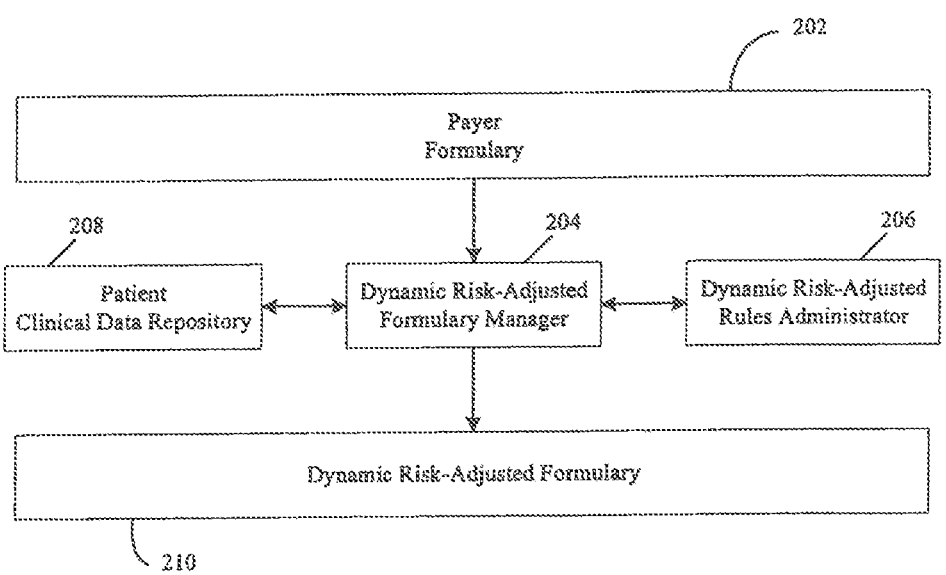
FIG. 4 is a block diagram that depicts high-level information flow in the creation of a dynamic formulary.

To this point, the formulary has been presented without regard to a patient's condition or other information relevant to a formulary. FIG. 4 depicts the flow of data in an embodiment of the invention referred to herein as the "Dynamic Risk-Adjusted Formulary Manager" (DRAFM), which augments static formularies with clinical or other data to provide dynamic formularies based on the rules provided by payers and PBMs and available patient data. In one embodiment, DRAFM comprises a set of technology components that allows physicians, payers, PBMs, or employers to specify rules that will assist in providing clinicians with formularies that are based on specific conditions of patients. In one embodiment, the workflow 200 starts when a request for a formulary 202 is made and the original formulary is run through a DRAFM 204 according to an embodiment of the invention. The DRAFM 204 checks to see if any rules apply to the formulary being prescribed. The rules are entered through the Dynamic Risk-Adjusted Rules Administrator 206, a software tool that may be Web-based, provided to physicians, payers, PBMs, and employers. If a rule exists, the DRAFM pulls the appropriate clinical data from a repository 208 and verifies it against the rule conditions. The modified formulary is the output 210 of the workflow.

The DRAFM 204 requests data needed to verify any applicable rules. When a rule requires a change in the original formulary, the rule number and text describing the rule will be provided so it can be recorded on the prescription. This will ensure proper processing of the prescribed medication throughout the entire workflow of the prescription.

Figure 5:
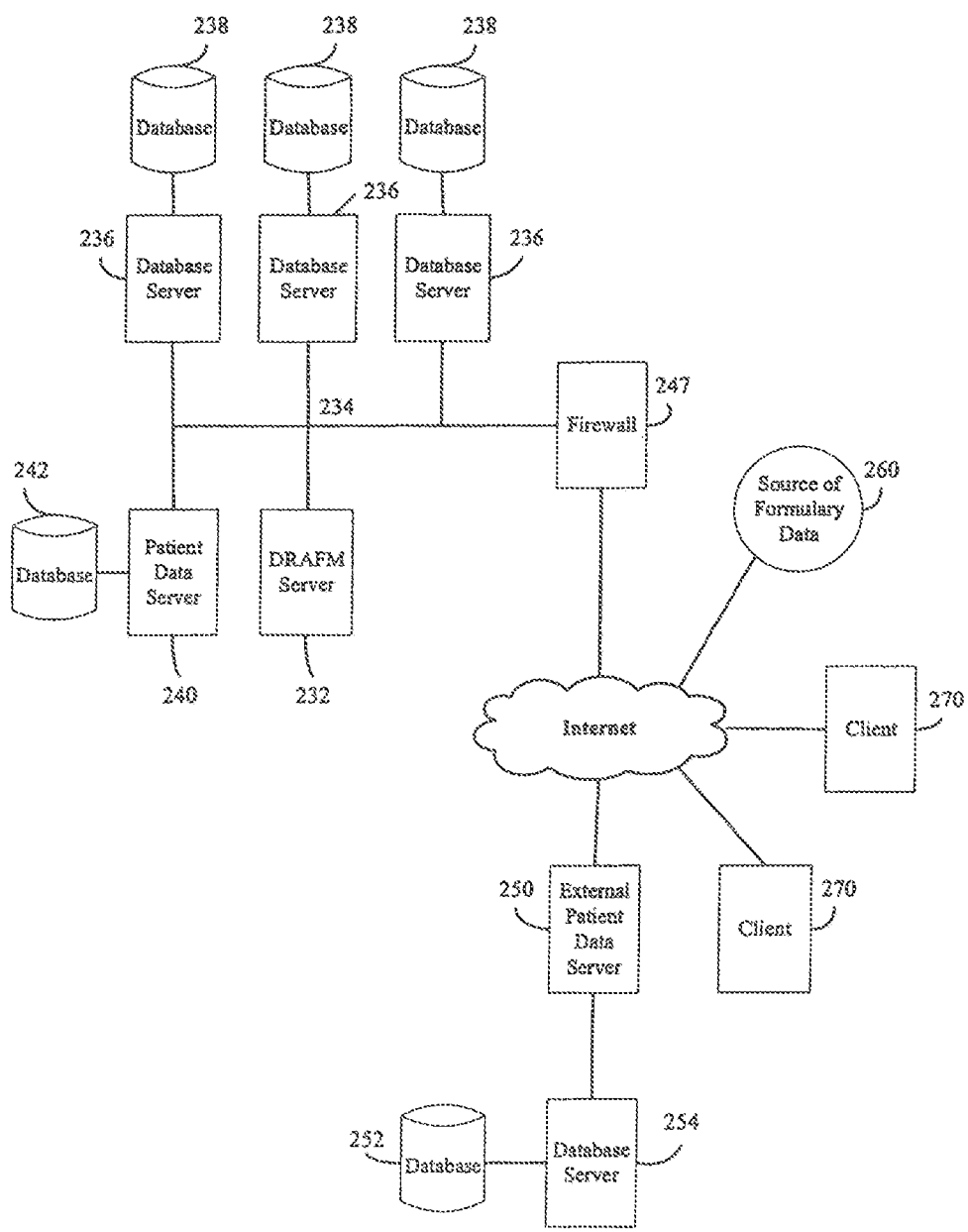
FIG. 5 is a block diagram depicting configuration of computers and networks suitable for implementing the invention.

FIG. 5 depicts an example of an architecture suitable for supporting a DRAFM such as the workflow depicted in FIG. 4.

A DRAFM itself may be embodied in computer software, software components, or both, executing on one or more servers 232. The server may be connected by one or more interconnected local area networks 234 to one or more database servers 236, each of which provides access to one or more databases 238. The local area network may also contain one or more systems 240 that provide access to patients' medical histories, which may be stored in one or more local databases 242.

In the embodiment represented by FIGS. 4 and 5, communication with other sources and consumers of information is achieved using the Internet 245. Access to the Internet may optionally be through one or more firewalls, gateways, or other security arrangements 247. Other means of communication may also be used instead of or in addition to the Internet, such as dial-up lines, dedicated leased lines, and private wide area networks.

In the embodiment represented by FIGS. 4 and 5, patient medical data may be obtained from one or more external sources, such as server 250, which itself has access to a database 252 through a database server 254.

As described above, the formulary data and rules, which the payers create, are provided to the embodiment represented by FIGS. 4 and 5 by PBMs, which distribute this information on the payers' behalf. In the embodiment, the data are received electronically from one or more sources 260.

References to the DRAFM are made by one or more clients 270. Clients will comprise electronic prescribing systems 174, electronic medical records providers 175, and systems for retail pharmacies 176, as discussed in connection with FIG. 3.

It will be appreciated by those skilled in the art that the architecture depicted in FIG. 4 is just one of many suitable for implementation of the invention. More than one component may be involved in performing one or more of the functions of the system, depending on the expected load and other factors. Functions depicted as being performed by separate components may in some implementations be performed by a single component, again, depending on the expected load and other needs of the system. Other configurations of servers and network topographies may work as well as those described here.

Figure 6:
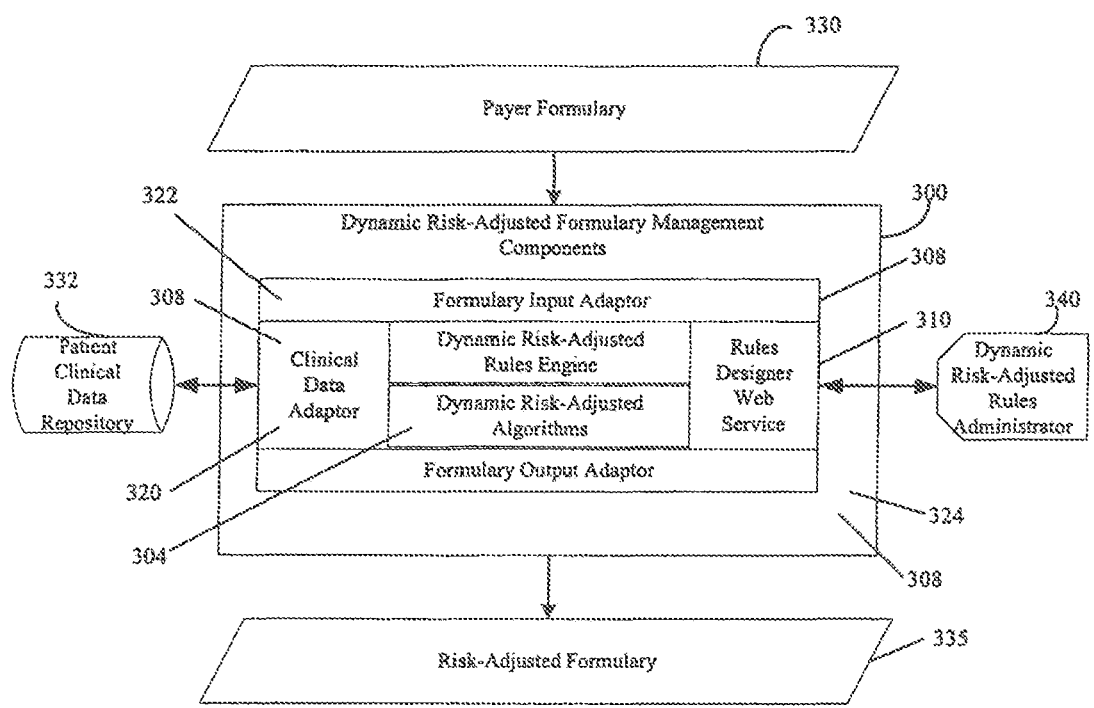
FIG. 6 is a diagram illustrating logical components suitable for implementing embodiments of the invention.

As illustrated in FIG. 6, the DRAFM 300 comprises the rules engine 302 and algorithms 304. They are responsible for verifying a existence of a rule, requesting data needed to validate a rule, and creating a new formulary based on the rule.

The DRAFM 300 also comprises interface components 308, referred to herein as adaptors, which are responsible for moving data in a standard format into and out of the DRAFM. The DRAFM 300 also comprises a set of web services 310 that will allow for the creation, modification, and deletion of the rules.

Web services is a well-known technology for making computing services available to other computers across a network. Requests and responses may use the XML-based Simple Object Access Protocol (SOAP), and interfaces may be defined using a standard called WSDL.

The algorithm 304 applies the rules to the clinical data at the time of prescribing. The algorithm tests for a rule, calls the appropriate adaptors, and produces the final formulary once the rules have been evaluated.

The rules engine 302 applies specific rules to numerous data items. It handles the conditional logic required to evaluate each item in connection with each request, modifying a generic formulary based on the data items and rules. Sometimes data will not be available despite being required to evaluate one or more rules respecting one or more specific formulary items. When that happens, the specific formulary item or items will not be changed, but flagged as associated with one or more rules that could not be validated.

The DRAFM adaptors 308 are directly responsible for moving data into and out of the algorithm and rules engine. In the embodiment depicted in FIG. 6, three adaptors provide this functionality: the clinical data adaptor 320, the formulary input adaptor 322, and the formulary output adaptor 324. Each is described below.

The formulary input adaptor 322 has two basic workflows. The interaction is started by a calling system (called the "Initiating System", not pictured), whereby the Initiating System identifies the payer and provider. The formulary input adaptor 322 checks to see if the specified payer and plan combination has any rules. If no rules exist, the response of the formulary input adaptor 322 confirms that fact, and no other transaction is needed. If one or more rules do exist, then the formulary input adaptor 322 requests the standard formulary 330 along with the patient's data. The formulary input adaptor 322 then transfers control with the information to the algorithm 304 and rules engine 302.

The clinical data adaptor 320 builds a request for data to evaluate a rule and accepts the result of that request. That result comprises clinical information used to verify the rule. The algorithm 304 makes the determination that a rule is present and requests the data from the clinical data adaptor 320. The clinical data adaptor 320 publishes the request for data to subscribed services of a clinical data repository 332. In the embodiment, the clinical data adaptor will request only the data that is needed to verify the specific rule. (As discussed in connection with FIG. 5, the repository may be stored in storage accessible by one or more servers 240 local to the DRAFM server 232, one or more remote servers 250, or both.) Upon receiving the request, the clinical data repository 332 resolves the request with the appropriate data. The exchange of information may be implemented using a conventional web service interface.

The formulary output adaptor 324 creates a response to be sent back to the Initiating System (not pictured). This response will include the newly-created dynamic risk-adjusted formulary 335, which reflects application of the rules defined by the payer.

The Dynamic Risk-Adjusted Formulary administrator 340 is an application, possibly web-based, that allows for the creation of the rules. This tool allows payers to enter and modify the rules directly. For security and privacy reasons, the Dynamic Risk-Adjusted Formulary administrator 340 authenticates users, who will have access only to rules applicable to their organization. Depending on the embodiment, different levels of access within an organization will be granted to control the ability to view, create, and modify rules.

In the embodiment, only certain kinds of patient information are available to the rules engine 302. The type of a particular piece of information also dictates the permissible kinds of comparisons that a rule may employ. The following table summarizes the types of data and the permissible tests associated with each data type:

| Clinical data type | Data contained | Tests permissible in rules |
|---|---|---|
| Medication | Drug code, dosage, duration | Exact matches |
| Lab result values | Specific analyte in a decimal number | Range or exact match |
| Diagnosis code | Specific diagnosis code representing ICD9 standard in a decimal number | Range or exact match |
| Blood pressure | Systolic and diastolic pressure as integers | Range or exact match |
| Height | Height in inches as an integer | Range or exact match |
| Weight | Weight in pounds as an integer | Range or exact match |
| Sex | A single character representing the sex of the person | Match or no match |

For example, a rule may depend on the drug code, the dosage, or duration of prescription for a medication, or any or all of those criteria, but may depend only on whether the clinical data matches a criterion exactly. In contrast, a rule may depend on the patient's height, and may specify either an exact match or a range of values.

The foregoing table is meant only to illustrate an embodiment of the invention and not to limit in any way the types of data that other embodiments may depend on or the conditions that such other embodiments may apply to those data.

Figure 7:
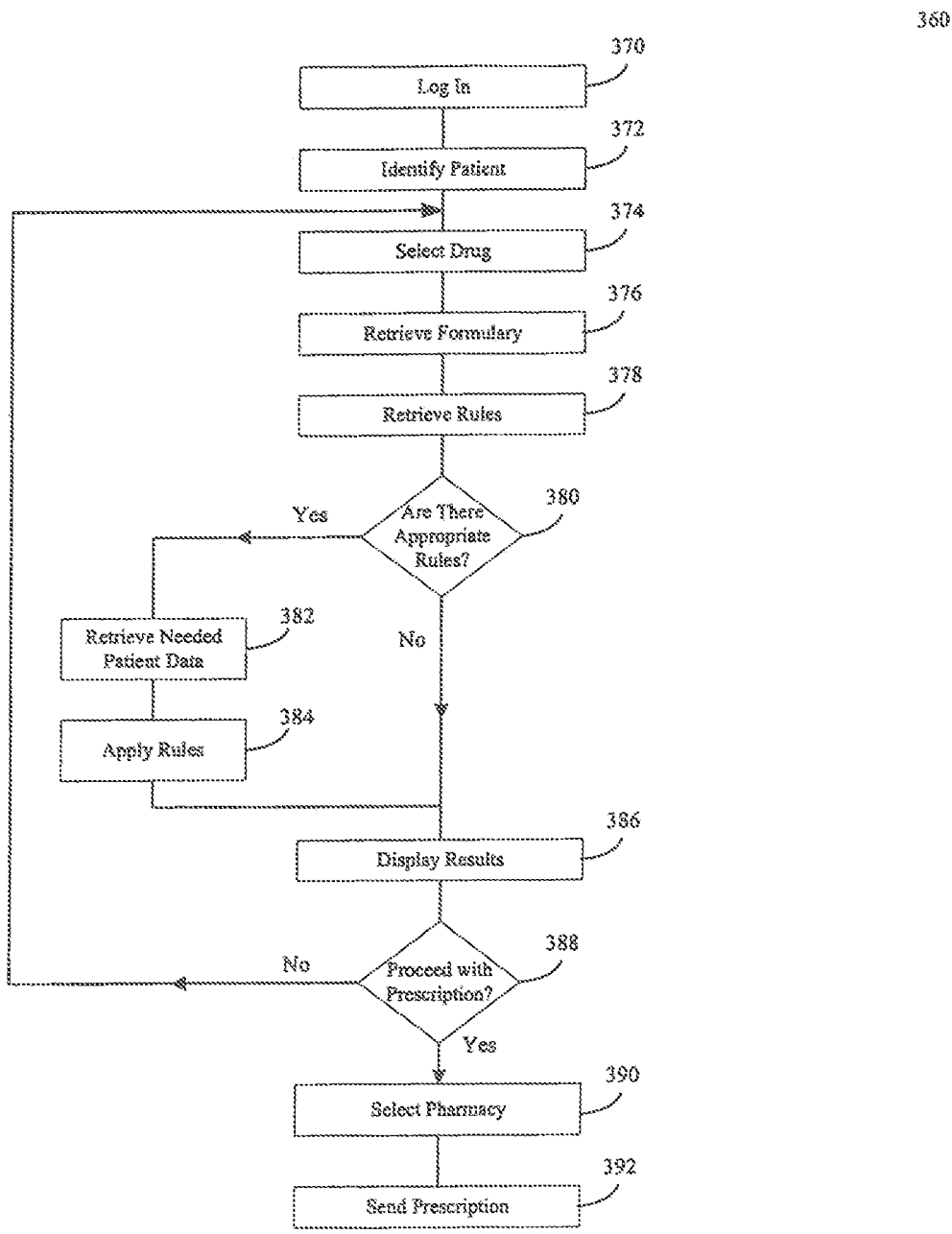
FIG. 7 depicts a workflow diagram in which a physician prescribes a drug according to an embodiment of the invention.

FIG. 7 depicts an embodiment of a workflow 360 as a prescriber prepares an electronic prescription on a system that incorporates reference to an embodiment of a DRAFM, such as, for example, the one depicted in FIG. 6. The prescriber must first login in block 370 to the electronic prescribing system, using some means of authentication to verify that the prescriber is the person with authority to access patients' records and to write a prescription.

Once the user has been allowed access to the system, the user then identifies in block 372 the patient for whom the prescription is being prepared. Because of the connection between the electronic prescribing system and the patient's electronic medical records, there will often be an existing record of the patient in the system, and that record will typically hold information about the patient's prescription coverage. That information will include the names or other identifying information of the PBM and the plan that covers the patient.

If the patient is new to the physician, such records may be created as part of the patient intake process.

In the next block 374, the prescriber selects a drug for the patient. In response, the system retrieves in block 376 an unadjusted (e.g., static) formulary that corresponds to the patient's payer and plan. It also retrieves in block 378 the rules specified by the payer and distributed by the PBM. The system passes this information to the algorithm 304 (FIG. 6).

The algorithm 304 checks in block 380 whether any rules apply to the current medication. If there are such rules, the algorithm retrieves in block 382 the clinical data needed to evaluate the rules and then transfers control to the rules engine 302 (FIG. 6). The rules engine 302 then applies in block 384 the rules to the clinical data. The algorithm gathers the results of these evaluations and uses them to modify the unadjusted formulary, producing the dynamic formulary for presentation in block 386 to the prescriber.

In some embodiments, the order in which functionality is performed may differ from that depicted in FIG. 6. For example, the order of blocks 374 and 376 may be reversed. In such embodiments, an entire formulary and all associated rules may first be downloaded, and then a prescriber may select a drug to prescribe.

If the check in block 380 reveals that no rules apply in a particular circumstance, then the DRAFM will, in the embodiment, return the unadjusted formulary to the electronic prescribing system.

Other information may be displayed in block 386 besides the results of applying the rules to the originally selected drug. In some embodiments, a list of other drugs may be presented to the prescriber alongside the selected drug, where those drugs may be medically appropriate for the patient. Such a listing will typically indicate whether each drug is or is not included in the patient's dynamic formulary.

Other information displayed at block 386 may include warnings about potential drug interactions discovered through referring to the patient's current clinical records.

Block 388 indicates whether the selected drug is on the patient's dynamic formulary or not. Depending on the specific embodiment, also indicated may be how much the patient will be expected to pay for this prescription and whether there are any conditions or limitations on the payer's willingness to cover that drug. Based on this information, the prescriber may proceed to prescribe the drug or may return to block 374 to select another drug.

Blocks 390 and 392 depict generation of a prescription once the prescriber has accepted the choice of drug. Depending on the implementation and the prescriber's preference, the prescriber may still write a prescription in the traditional manner, using a pen and prescription pad. (Regardless of the means by which a prescription is generated, the prescriber retains the ability to prescribe any drug, regardless of whether the drug is on the applicable formulary or not.) But, for the sake of efficiency and accuracy, the prescriber may transmit the prescription electronically to a retail pharmacy, which will in turn dispense the drug. A pharmacy that is to receive the prescription is first selected in block 390. The prescriber may then send the prescription electronically in block 392 to the pharmacy.

Figure 8:
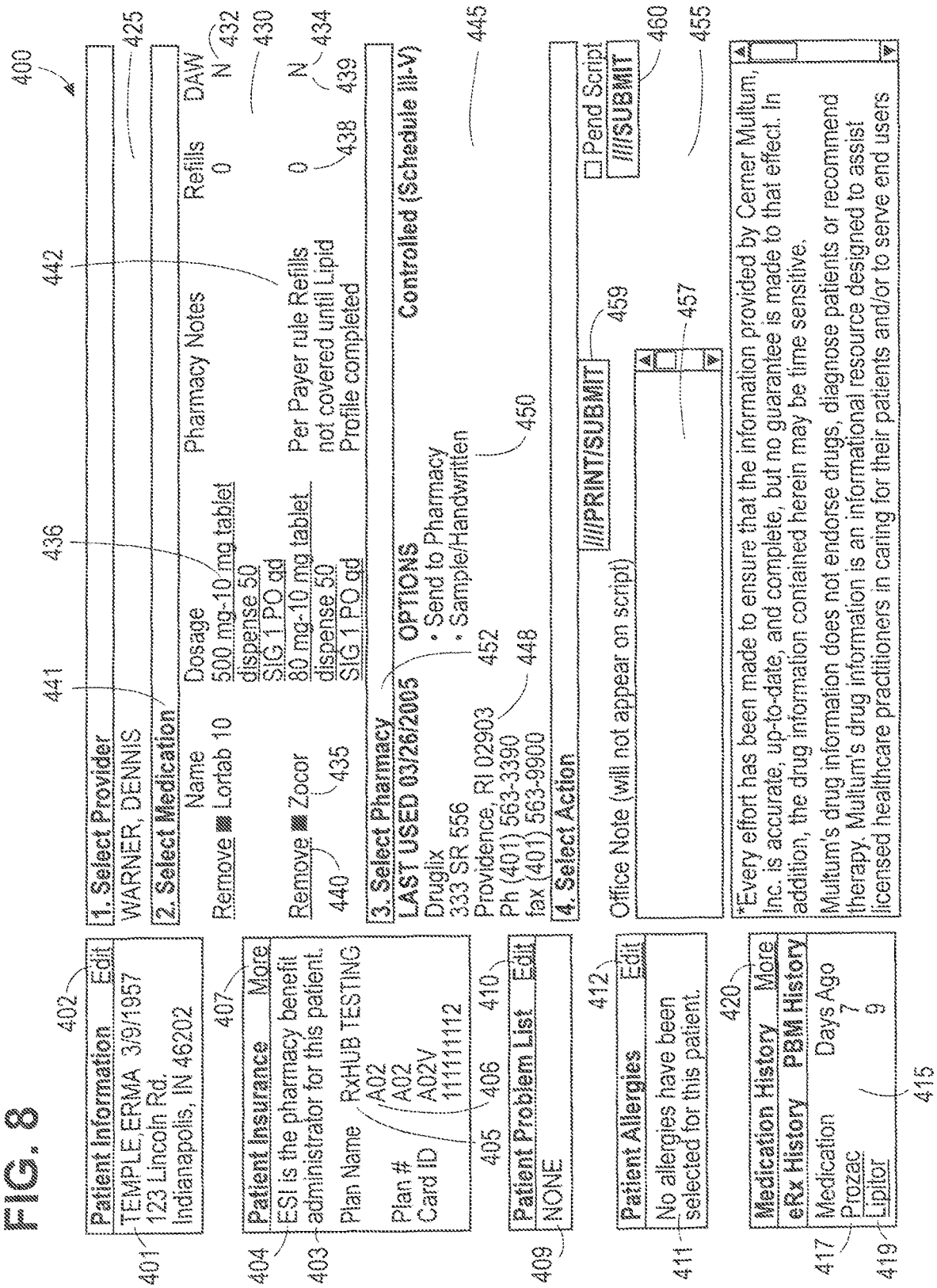
FIG. 8 depicts a user interface screen for use in preparing electronic prescriptions according to an embodiment of the invention.

FIG. 8 depicts a user interface 400 to an electronic prescribing system that incorporates the functionality of the DRAFM 204 (FIG. 4). In the embodiment, the electronic prescribing system is web-based, so this interface appears within a Web browser, such as Microsoft's Internet Explorer. The user interacts with this interface through standard computer input means, which may comprise a computer mouse and a keyboard.

At the highest level, the interface 400 is divided into two regions. Information about the patient appears in a region running along the left side of the interface. The rest of the interface is related to the prescription or prescriptions being generated.

In the upper left-hand corner of the interface 400, region 401 presents the patient's name and address. Hyperlink 402 leads to an interface for editing this information.

Below region 401, in region 403, the patient's insurance information appears. This includes the name of the PBM 404, the name of the patient's plan 405, and other information 406, comprising, for example, the plan, group, and card numbers. Hyperlink 407 leads to an interface for editing the insurance information.

Below the insurance information in region 403 is a region 409 where any diagnosed problems of the patient are listed. Hyperlink 410 leads to an interface for editing this list. Similarly, below the insurance information region 409 is a region 411 listing the patient's known allergies. Hyperlink 412 leads to an interface for editing the list of allergies.

Region 415 displays the patient's medication history, gathered from sources including the prescriber's own electronic medical records, the records of the electronic prescribing system, and the records of participating PBMs. The records 417, 419 are displayed as a list of hyperlinks, each leading to a display of more information about the patient's use of the medication. Hyperlink 420 leads to a display of more information from the patient's medication history, including more detail about displayed prescriptions and, in some embodiments, prescriptions given in the past but that have been discontinued.

Region 425 in FIG. 8 may allow the user to select the prescriber associated with the current prescriptions. In some embodiments, the identify of the prescriber will be fixed at login time through association with the identity of the logged-in user. In others, a hyperlink is provided that leads to an interface allowing the user to change the identity of the provider associated with the prescriptions. Such an interface may require the user to prove that the user is authorized to enter prescriptions on that provider's behalf.

Region 430 displays the prescriptions 432, 434 that the prescriber has entered for this patient. Each prescription appears on a separate line that discloses the name of the drug 435, the dosage and form in which the drug is to be dispensed 436, the number of refills authorized 438, and whether the prescription must be "Dispensed as Written" ("DAW") or the pharmacist may substitute a less expensive generic drug for a branded version 439. Each listing also has a hyperlink 440 allowing the prescription to be deleted. Hyperlink 441 leads to an interface (depicted in FIG. 9) allowing the prescriber to add another medication.

If the rules of the dynamic formulary restrict payment for the drug, that information will appear within this region at 442. In the displayed example, the formulary rules have examined the patient's clinical records and have not found a required blood test. According to the rules in this case, the patient's plan will cover a thirty-day supply of the drug, but will not cover refills until the patient's record reflects that the test has been done.

Region 445 in FIG. 8 displays information about the pharmacy to which the prescription will be sent. In the embodiment, the information includes the pharmacy's names, address, and phone number 448.

In some instances, a prescriber will create an entry for an electronic prescription but will not want to send the prescription itself electronically to a pharmacy. For instance, the prescriber may write a prescription by hand but nonetheless want the prescription to be cleared against the patient's dynamic formulary and recorded in the patient's electronic medical records. Control 450 allows a prescriber to indicate that a particular prescription should be thus entered into the electronic records but not sent to a pharmacy.

Hyperlink 452 in FIG. 8 leads to an interface allowing the user to change the selected pharmacy.

Once the prescriber is satisfied that the electronic prescriptions and related information are correct, region 455 contains controls for submitting the prescriptions. For the prescriber's own records, a text input region 457 allows entry of notes that will be stored, but not send to the pharmacy. Control 459 allows the user to submit an electronic prescription to the selected pharmacy and automatically print a hard copy locally. Control 460 gives the user the alternative of submitting the electronic prescription electronically without printing a hard copy.

Other types of user interfaces are possible. The configuration depicted in FIG. 8 is referred to in the art as a "thin client," because the Web browser, which presents the user interface, performs little or no additional processing besides displaying the interface and sending user input back to the server that hosts the electronic prescribing system. Other embodiments may use so-called "thick clients," which may comprise an electronic prescribing application running on one or more personal computers at a prescriber's location and exchanging processed information with one or more remote servers.

FIG. 9 depicts a user interface 480 for selecting a drug to prescribe, which is accessed through hyperlink 441 of user interface 400 depicted in FIG. 8. The interface 480 includes a text input region 427 in which the user may enter the name of a drug to prescribe. Some embodiments may allow the user to enter a partial name and search for all drugs that match. Control 428 allows the user to execute the search. Control 429 allows the user to cancel the search and return to user interface 400 depicted by FIG. 8.

A list 432 of drugs recently selected for a concerned patient may be displayed as in FIG. 9 for the user's convenience. Where appropriate, an entry on the list will disclose restrictions 435 on prescribing the drug, based on the patient's dynamic formulary.

Once the user has selected the drug, a user interface (not pictured) is presented allowing the user to selected the form, dosage, and frequency of the prescription. In some embodiments, that user interface will also display a list of drugs similar to the selected drug with formulary information for each such listed drug.

Figure 10:
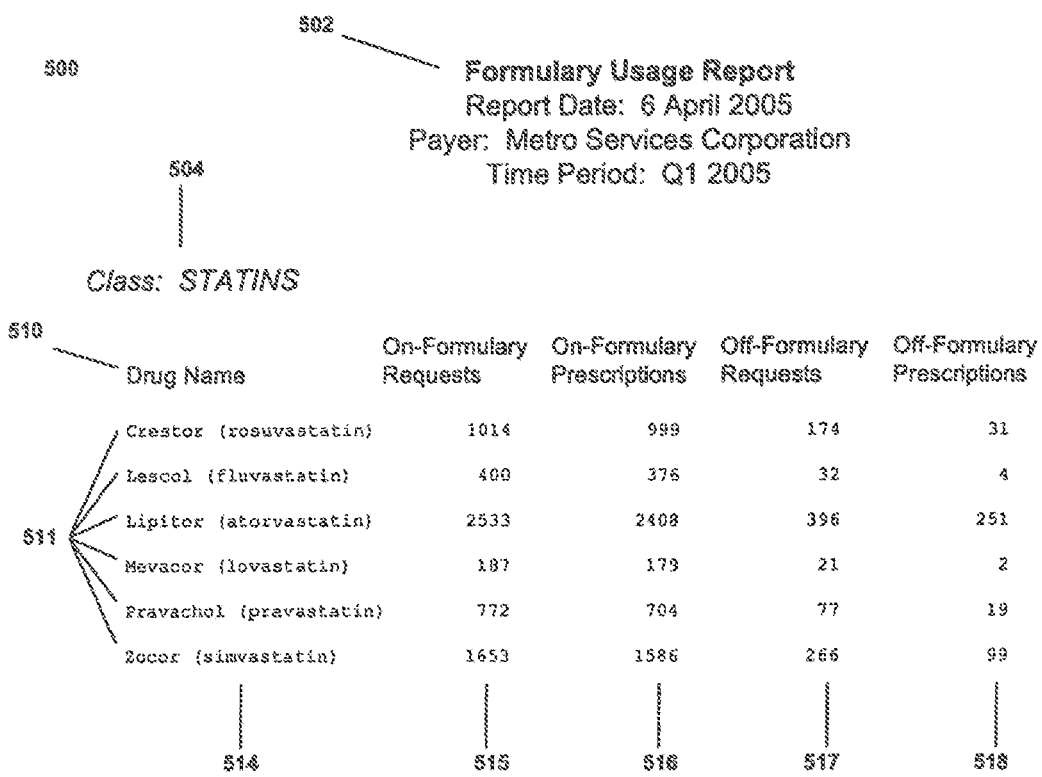
FIG. 10 is a report that may be generated in an embodiment of the invention.

FIG. 10 depicts an example of a report 500 that may be generated by an embodiment of the invention. The report 500 comprises information about the number of prescriptions that were written in the first calendar quarter of 2005 for drugs called "statins," which are prescribed frequently to reduce blood cholesterol.

The example report 500 begins with a header 502 that indicates the nature and contents of the example report. This header 502 indicates that the report was generated on Apr. 6, 2005, and reports data gathered between Jan. 1, 2005, and Mar. 31, 2005. In generating the report, only prescriptions for which the payer was Metro Services Corporation are included.

A subheader 504 indicates that this report describes only prescriptions for statins.

In this example, the report data appear as a table, with a header row 510 describing what each column represents and then a separate row 511 for each drug listed in the table. In each row 511, the table lists the brand and generic names 514 of the drug. The rest of the data in each row relate to how often prescribers chose drugs that were on their patient's formularies. The table indicates the number of times each drug was requested and found to be on the formulary 515, the number of times that drug was prescribed from the formulary 516, the number of times the drug was requested and found not to be on the formulary 517, and the number of times that the drug was prescribed despite not being on the formulary 518.

The statistical data presented in the report 500 may be the result of processing logging data gathered during operation of an embodiment. For example, implementations of some or all of the blocks that comprise the workflow 360 depicted in FIG. 7 may be adapted to include logging of their functions. An embodiment may be adapted to begin collecting logging data associated with every login session, beginning in block 370 (FIG. 7). Such logging data may be stored in the memory of one or more computers and/or in a database. As another example, a record in memory and/or a database may be created when a prescriber selects a drug in block 374 (FIG. 7), such record containing the name of the requested drug; and the formulary data displayed in block 386 may also be added to the record, along with the prescriber's decision in block 388 (FIG. 7). When the end of the workflow is reached in block 392 (FIG. 7), any records containing log data that remain in memory may be written to a database or other storage medium. The process of collection and storage of the log data may include association of data about one or more patients, prescribers, plans, payers, formularies, and/or medical records with the log data.

Generation of a report 500 as depicted in FIG. 10 may involve retrieval and processing of log data gathered as described above to produce the statistics that appear in the report 500. Such retrieval may involve conventional SQL queries performed on one or more relational databases. Processing may then involve examination of one or more data sets resulting from such a query and/or accumulation of statistical data.

It will be appreciated by one skilled in the art that reports provided in accordance with the invention may vary widely depending on the particular embodiment used and the users' needs. Accordingly, FIG. 10 is intended only to illustrate one possible type of report and is not to limit the scope, contents, or appearance of any reports that may be provided according to the invention.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modifications are intended to be included within the scope of the invention. Except to the extent necessary or inherent in the processes themselves, no particular order to steps or stages of methods or processes described in this disclosure, including the Figures, is implied. In many cases the order of process steps may be varied without changing the purpose, effect or import of the methods described.

The invention claimed is:

1. A method of providing dynamic formulary information in real time during electronic prescribing, comprising:
   storing in a network-based non-transitory storage device formulary information that is associated with a patient and comprises at least one rule and a first formulary, the first formulary comprising information about payment by a payer for one or more drugs;
   providing remote access to clients over a network so any one of the clients can request formulary information in real time in the course of creating an electronic prescription;
   receiving from one of the clients over the network a request for formulary information pertaining to the patient and to one or more medications;
   in response to receiving the request for formulary information, automatically retrieving medical information comprising at least one record of a patient from a first electronic information source over the network;
   receiving the medical information in a standardized format from an adaptor;
   in response to receiving the request for formulary information, automatically generating by a dynamic risk-adjusted formulary manager (DRAFM) server a dynamic second formulary, comprising information about payment by the payer for one or more drugs by applying the at least one rule to the standardized medical information and the first formulary;
   storing the second formulary in the DRAFM server;
   automatically generating a message, by an adaptor in communication with the DRAFM server, containing information from the second formulary in response to the request for formulary information; and transmitting the message to the client in real time, so that the client has immediate access to dynamic formulary information.

2. The method of claim 1, wherein the message containing information from the second formulary includes first information that identifies at least one drug that is in the second formulary and second information that identifies at least one drug that is not in the second formulary.

3. The method of claim 2, wherein the second information includes identification of at least one reason for exclusion of at least one of the drugs that is not in the second formulary.

4. The method of claim 2, wherein the second information includes identification of at least one condition such that if the at least one condition is fulfilled, then at least one of the drugs that is not in the second formulary before fulfillment of the condition will be in the second formulary after fulfillment of the condition.

5. The method of claim 4, wherein at least one of the conditions includes subjecting the patient to a medical test.

6. The method of claim 1, wherein:

the request for formulary information identifies a candidate drug; and the message containing information from the second formulary includes indication that the candidate drug is not in the second formulary and identification of at least one alternate drug that is on the second formulary and may be prescribed instead of the candidate drug.

7. The method of claim 1, wherein the at least one rule includes at least one conditional rule that depends on the medical information.

8. The method of claim 7, wherein at the at least one conditional rule includes at least one rule that depends on the age of the patient.

9. The method of claim 7, wherein at the at least one conditional rule includes at least one rule that depends on the sex of the patient.

10. The method of claim 7, wherein at the at least one conditional rule includes at least one rule that depends on one or more records of medical tests performed upon the patient.

11. The method of claim 7, wherein at the at least one conditional rule includes at least one rule that depends on one or more records of diagnosed medical conditions associated with the patient.

* * * * *